United States Patent [19]

Verduijn et al.

[11] Patent Number: 4,894,214
[45] Date of Patent: Jan. 16, 1990

[54] ZEOLITE L PREPARATION

[75] Inventors: Johannes P. Verduijn, Spijkenisse; Pieter E. Gellings, Oostvoorne, both of Netherlands

[73] Assignee: Exxon Research & Engineering Company, Florham Park, N.J.

[21] Appl. No.: 160,362

[22] Filed: Feb. 25, 1988

[30] Foreign Application Priority Data

Feb. 25, 1987 [GB] United Kingdom ............... 8704365
Jan. 4, 1988 [GB] United Kingdom ............... 8800051

[51] Int. Cl.4 ............................................. C01B 33/28
[52] U.S. Cl. ..................................... 423/328; 423/329
[58] Field of Search ............... 423/326, 328, 329, 330; 502/60, 77

[56] References Cited

U.S. PATENT DOCUMENTS 3,216,789 11/1965 Breck et al. .......................... 423/328
4,309,313 1/1982 Barrett et al. ........................ 423/328
4,544,539 10/1985 Wortel .................................. 423/328
4,554,146 11/1985 Vaughan .............................. 423/328

FOREIGN PATENT DOCUMENTS 0142355 5/1985 European Pat. Off. ........... 423/328
0185519 6/1986 European Pat. Off. ........... 423/328
909264 10/1962 United Kingdom ............... 423/328

Primary Examiner—Robert L. Stoll
Assistant Examiner—R. Bruce Breneman
Attorney, Agent, or Firm—S. H. Markowitz

[57] ABSTRACT

Zeolite L containing caesium is prepared by a process in which said zeolite L is crystallized from a synthesis mixture with a molar composition (expressed as oxides) of:

$K_2O/SiO_2$: 0.15 to 0.40
$K_2O/Cs_2O$: 3 to 10
$H_2O/K_2O$: 40 to 100, and
$SiO_2/Al_2O_3$: 7 to 13 and containing 0.5 to 15 ppm (by weight) of divalent metal carbons, e.g. Mg ions. The zeolite L can form part of a dehydrocyclization and/or isomerization catalyst.

6 Claims, 3 Drawing Sheets

ZEOLITE L PREPARATION

This invention relates to the preparation of zeolite L

BACKGROUND OF THE INVENTION

Zeolite L has been known for some time as an adsorbant, and in U.S. Pat. No. 3,216,789 is described as an aluminosilicate of the formula:

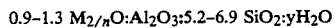

0.9–1.3 $M_{2/n}O:Al_2O_3:5.2$–$6.9\ SiO_2:yH_2O$ (where M is an exchangeable cation of valency n and y is from 0 to 9) having a characteristic X-ray diffraction pattern. The preparation of zeolite L is described in U.S. Pat. No. 3,216,789, EP-A-Nos. 167755, 142355, 142347, 142349, 109199, PL-A-No. 72149, U.S. Pat. No. 3,867,512, and SU-No. 548567.

EP-A-No. 96479 describes and claims zeolite L having a characteristic morphology and size, which is particularly valuable for use as a catalyst base in hydrocarbon conversions such as aromatisation, and comprising crystallites in the form of cylinders with a mean diameter of at least 0.1 micron, preferably at least 0.5 micron.

EP No. 96479 describes a synthesis of zeolite L which is conducted so that the amount of the contaminant zeolite W, which is know to grow in such a system as a competitive phase, is minimised. A preferred synthesis gel described in EP 96479 has the following mole ratios:

$2.62K_2O_3:10SiO_2:160H_2O$ and it is discussed how this gel may be varied by changing the molar amount of one component within the following ranges:
K$_2$O: 2.4–3.0 moles
Al$_2$O$_3$: 0.6–1.3 moles
SiO$_2$: 8–12 moles
H$_2$O: 120–240 moles
EP-A-142353, EP-A-142354 and EP-A-185519 describe developments of this process for forming cylindrical zeolite L.

Zeolite L may be used as a catalyst base in aromatisation reactions. U.S. Pat. No. 4,104,320 discloses dehydrocyclisation of aliphatic compounds in the presence of hydrogen using a catalyst comprising zeolite L and a group VIII metal. The particular zeolite disclosed in EP No. 96479 is remarkably effective in such aromatisation reactions being capable of forming catalysts which have extended lifetime. Such dehydro- cyclisation and/or aromatisation reactions and catalysts for use in such reactions are also described in EP-A-Nos. 107389, 184451, 142351, 145289, 184450, U.S. Pat. No. 4,614,834, GB-A-Nos. 2116450, 2114150, U.S. Pat. Nos. 4,458,025, 4,456,527, GB-A-Nos. 2142648, 2106483, U.S. Pat. No. 4,443,326, GB-A-Nos. 2121427, 2153840, 2153384, U.S. Pat. Nos. 4,517,306, 4,539,304, 4,539,305, 4,547,472, GB-A-No. 2166972, U.S. Pat Nos. 4,579,831, 4,608,356 and EP-A-No. 201856.

SUMMARY OF THE INVENTION

It has been found that the potassium form of zeolite L herein identified as zeolite KL shows enhanced properties as an aromatisation catalyst if it also contains some caesium. However attempts to replace some of the potassium ions by caesium ions in the preparation of zeolite KL have not been very successful in the past as the presence of caesium ions favours the formation of pollucite rather than zeolite L. We have now found a method of incorporating caesium in the zeolite KL without any substantial formation of pollucite.

DETAILED DESCRIPTION OF THE DRAWING

Figure 1:
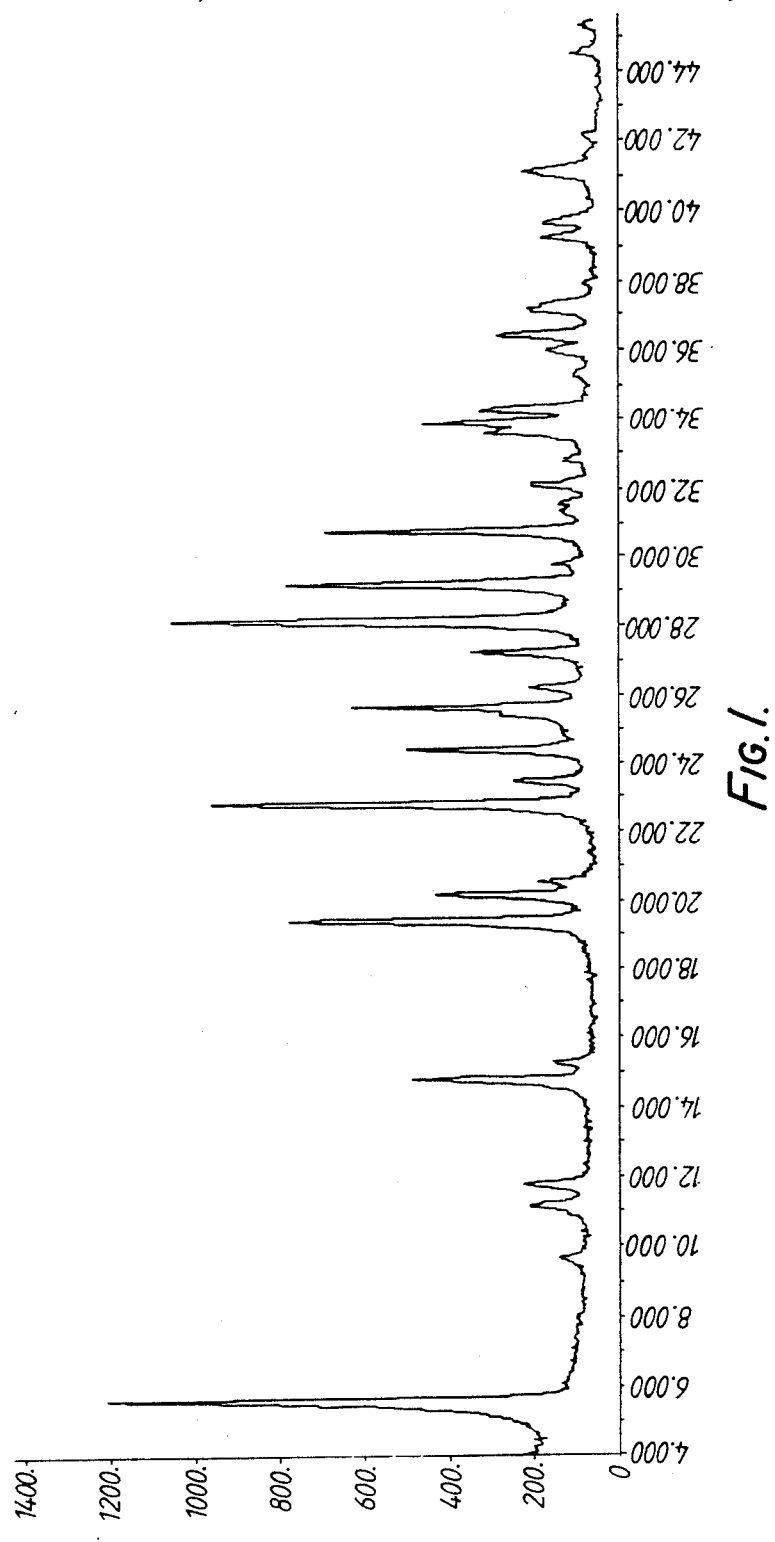
FIG. 1: x-ray diffractogram of the product of Example 1.

According to this invention zeolite L containing caesium can be obtained by a process in which said zeolite L is crystallised from a synthesis mixture with a molar composition (expressed as oxides) of:
K$_2$O/SiO$_2$: 0.15 to 0.40
K$_2$O/Cs$_2$O: 3 to 10
H$_2$O/K$_2$O: 40 to 100 and
SiO$_2$/Al$_2$O$_3$: 7 to 13
and containing at least 0.5 ppm (by weight) of divalent metal cations, e.g. magnesium ions.

It was surprisingly found that the incorporation in the synthesis mixture of very small quantities of divalent metal cations enables one to obtain substantially only zeolite L in which part of the potassium is replaced by caesium rather than zeolite L containing large amounts of by-products such as pollucite, erionite and zeolite W.

The synthesis mixture is conveniently derived from the admixture of two solutions—Solution A and Solution B.

Solution A can be termed a potassium—caesium aluminate solution and Solution B can be termed a silicate solution containing divalent metal cations.

The source of potassium is usually potassium hydroxide, e.g. as pellets.

The caesium can be introduced as the hydroxide or as a salt, e.g. a halide such as CsCl.

The source of aluminium may be an alumina introduced into the reaction medium as, for example, Al$_2$O$_3$.3H$_2$O, previously dissolved in alkali. However, it is also possible to introduce aluminium in the form of the metal, which is dissolved in alkali.

Thus Solution A may be formed from KOH or K$_2$O, CsOH.H$_2$O or CsX, Al(OH)$_3$ and water where X is a halogen such as chlorine or a nitrate.

The source of silicon for Solution B is generally silica, and this is usually most conveniently in the form of a colloidal suspension of silica such as Ludox HS 40 available from E. I. Dupont de Nemours and Co. Colloidal silica sols are preferred since they result in less contaminating phases. However, other forms such as silicates may be used.

The divalent metal may be a Group Ib metal such as copper, a Group II metal, for example magnesium, calcium, barium or zinc, Group IV metal such as lead, or Group VI, VII or VIII metals such as chromium, manganese, iron, cobalt or nickel. These metals may be introduced in the form of any convenient compound, for example as an oxide, hydroxide, nitrate or sulphate.

Thus Solution B may be formed from silica, a divalent metal salt, e.g. Mg(NO$_3$)$_2$ and water.

Solution A can be conveniently formed from a mixture of (1) KOH, (2) CsOH or CsX where X is halogen or nitrate, (3) Al(OH)$_3$ and (4) water.

In practice the aluminium hydroxide can be dissolved in Solution A by boiling and after cooling to ambient temperature, the weight loss of water due to evaporation may be corrected.

Solution B can be conveniently formed from a mixture of Ludox HS-40($SiO_2$) and water.

The relative quantities of Solutions A and B are such that the mole ratio of $SiO_2$ to $Al(OH)_3$ or $Al_2O_3$ is preferably between 7 and 13 e.g. about 10.

The overall synthesis mixture, e.g. obtained by transferring Solution A to Solution B and mixing the combined solutions, according to the invention has the molar composition (expressed as oxides) of:

$K_2O/SiO_2$: 0.15 to 0.40
$K_2O/Cs_2O$: 3 to 10
$H_2O/K_2O$: 40 to 100 and
$SiO_2/Al_2O_3$: 7 to 13 and containing at least 0.5 ppm (by weight) of divalent metal cations. Optionally these ratios are $K_2O/SiO_2$: 0.18 to 0.36 preferably about 0.2 to 0.26, e.g. about 0.22
$K_2O/Cs_2O$: 4 to 7 preferably 5 to 6.5, e.g. about 6.1
$H_2O/K_2O$: 70 to 90 preferably 75 to 85 e.g. about 80 and
$SiO_2/Al_2O_3$: 8 to 12 preferably 9 to 11 e.g. about 10 and containing 0.5 to 15, e.g. about 10 ppm (by weight) of divalent metal cations.

After mixing Solutions A and B for a period of time, e.g. about 4 minutes, to homogenise the mixture, the mixture is crystallised.

The crystallisation is generally carried out in a sealed autoclave and thus at autogenous pressure. It is generally inconvenient, although possible, to employ higher pressures. Lower pressure will require longer crystallisation times.

Crystallisation time is related to the crystallisation temperature. The crystallisation is usually carried out at a temperature of at least 130° C., preferably in the region of 150° C. and at this temperature the crystallisation time may be from 16 to 96 hours, typically from 40 to 80 hours. Lower temperatures may require much longer times to achieve good yield of the desired product, whereas times of less than 16 hours are possible when higher temperatures are used. A time of 60 to 70 hours is typical for a temperature of about 50° C.

Following the preparation as described above the zeolite KL containing caesium may be separated, washed and dried. The washing may be to a pH of more than 7, e.g. 9 to 10. Drying may be at a temperature of above 120° C., e.g. about 150° C. for about 16 hours.

Scanning electron micrographs (SEM) of the products of the invention show that they consist of cylindrical crystals with a length of between 0.5 and 1 micrometer and with a diameter of between 0.2 and 0.4 micrometers and no amorphous gel particles could be seen.

The zeolites formed in the process of the invention are preferably aluminosilicates and are described herein in terms of aluminosilicates, though other elemental substitutions are possible, for example aluminium may be substituted by gallium, boron, iron and similar di- or trivalent elements capable of existing in tetrahedral coordination, and silicon may be substituted by elements such as germanium or phosphorus.

The zeolite L formed by the invention may provide extended catalyst life when used as catalyst bases for aromatisation catalysts.

The zeolite L prepared by the invention may be used as a catalyst base and may be used in combination with a catalytically active metal in a wide variety of catalytic reactions. It is especially suited to catalytic applications where a low acid site strength is advantageous such as aromatisation.

The catalytically-active metal(s) may be, for example, a Group VIII metal such as platinum, or tin or germanium as described in U.S. Pat. No. 4,104,320, or a combination of platinum and rhenium as described in GB-A-No. 2004764 or BE-A-No. 888365. In the latter case, the catlyst may for appropriate circumstances also incorporate halogen as described in U.S. Pat. No. 4,165,276, silver as described in U.S. Pat Nos. 4,295,959 and 4,206,040, cadmium as described in U.S. Pat. Nos. 4,295,960 and 4,231,897 or sulphur as described in GB-A-No. 1600927.

A particularly advantageous catalyst composition incorporates from 0.1 to 6.0 wt. %, (based on the total weight of the composition), preferably from 0.1 to 1.5 wt. % platinum or palladium, since this gives excellent results in aromatisation. From 0.4 to 1.2 wt. % platinum is particularly preferred. Accordingly the invention provides a catalyst comprising the zeolite and a catalytically-active metal.

It may also be useful to incorporate into the catalyst of the invention one or more materials substantially inert under the conditions in which the catalyst is to be employed to act as a binder. Such binders may also act to improve the resistance of the catalyst to temperature, pressure and attrition.

The zeolite L of the invention may be used in a process for the conversion of a hydrocarbon feed in which the feed is contacted with a catalyst as described above under appropriate conditions to bring about the desired conversion. They may, for example, be useful in reactions involving aromatisation and/or dehydrocyclisation and/or isomerisation and/or dehydrogenation reaction. They are particularly useful in a process for the dehydrocyclisation and/or isomerisation of aliphatic hydrocarbons in which the hydrocarbons are contacted at a temperature of from 370° to 600° C., preferably 430° to 550° C., with a catalyst comprising zeolite L of the invention, preferably having at least 90% of the cations as potassium ions, and preferably incorporating at least one Group VIII metal having dehydrogenating activity, so as to convert at least part of the aliphatic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred embodiment the feed to a process for preparing aromatic hydrocarbons and particularly benzene comprises hexanes. The temperature of the catalytic reaction may be from 370° to 600° C., preferably 430° to 550° C. and preferably pressures in excess of atmospheric are used, for example up to 2000 KPa, more preferably 500 to 1000 KPa. Hydrogen is employed in the formation of aromatic hydrocarbons preferably with a hydrogen to feed ratio of less than 10.

The process is preferably otherwise carried out in the manner described in U.S. Pat. No. 4,104,320, BE-A-No. 888365, EP-A-Nos. 0040119, 0142351, 0145289 or 0142352.

The invention is now described with reference to the following Examples.

EXAMPLE 1

A synthesis mixture with a molar composition of:

2.20 K$_2$O/0.36 Cs$_2$O/Al$_2$O$_3$/10 SiO$_2$/161 H$_2$O and containing 9 wt ppm of Mg$^{2+}$ was prepared as follows:

Solution A: Potassium - Caesium Aluminate solution: (weight of reactants in grams)
KOH pellets (87.3% purity): 28.26
CsOH.H$_2$O powder (laboratory grade purity): 12.00
Al(OH)$_3$ powder (purity 98.6%): 15.80
H$_2$O: 75.12

Solution B: Silicate solution containing Mg$^{2+}$:
Ludox Hs-40 (SiO$_2$): 150.26
Mg(NO$_3$)$_2$ - stock solution: 75.05
H$_2$O: 40.00

The aluminium hydroxide was dissolved by boiling and after cooling to ambient temperature the weight loss due to evaporation of the water was corrected. The Mg(NO$_3$)$_2$ - stock solution, containing 0.048 mg Mg$^{2+}$/gram, was mixed with the Ludox. The solution A was quantitatively transferred to the solution B and the combined solutions were mixed for 4 minutes to homogenize the mixture. Of this mixture 331.54 gram was transferred to a 300 ml stainless steel autoclave and was crystallised for 65 hrs at 150° C. The resulting product was washed with 4 portions of 500 ml of water until a pH of 10.4 was obtained. The product was dried at 150° C. The amount of product obtained was 51.5 grams. This corresponds with a product yield, $$\left( \frac{\text{weight of dry product}}{\text{weight of gel}} \times 100\% \right)$$

based on the weight of the gel, of 15.5%. The product yield obtained from a similar synthesis mixture in which potassium is the only alkali source is 15.0%. XRD showed that the product was pure zeolite-L, the XRD crystallinity versus a standard zeolite was 56%. A similar zeolite-L product having the same crystallite size/morphology and synthesized in the potassium form would have an XRD-crystallinity of between 90 and 95% versus the same standard zeolite L. The low XRD-crystallinity of the example product is believed to be the result of the presence of Cs in this product.

SEM micrographs showed that the product consisted of cylindrical crystals with a length between 0.5 and 1 micron and with a diameter between 0.2 and 0.4 microns, no amorphous gel particles could be seen.

EXAMPLE 2 (COMPARATIVE)

An identical synthesis mixture, prepared in the same way but not containing added Mg$^{2+}$ was crystallised for 65 hrs at 150° C. The product was washed and dried using the same procedure/conditions as for Example 1. XRD showed that the product was contaminated with zeolite erionite and with zeolite-W. The XRD crystallinity vs the standard was 35%. SEM micrographs showed that the product consisted of cylinderlike particles with a length of about 3 microns and with a diameter of 1 to 1.5 microns. SEM micrographs also showed that the erionite was not present as a separate phase but was intergrown with the L-crystals. The presence of zeolite-W and pollucite was also confirmed by SEM.

Figure 2:
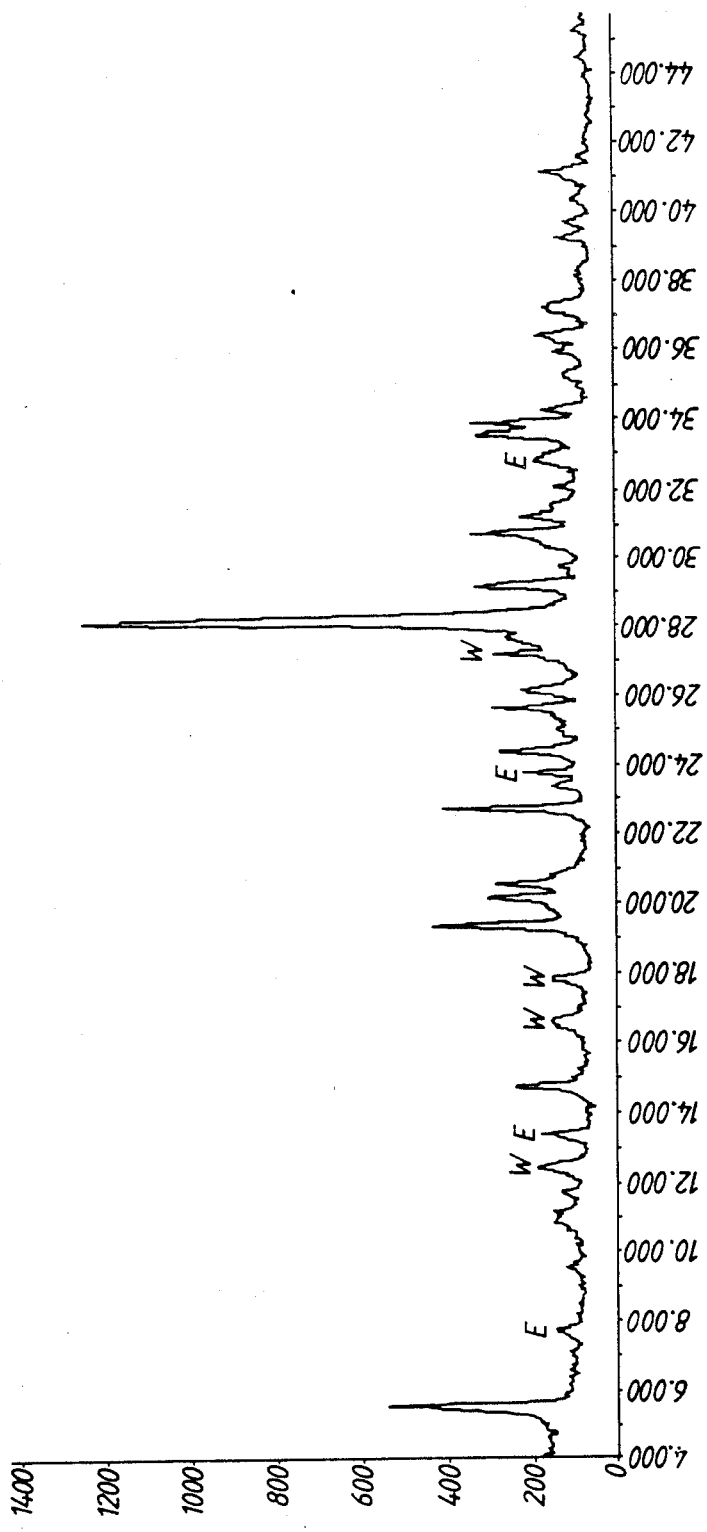
FIG. 2: x-ray diffractogram of the product of Example 2.
Figure 3:
FIG. 3: Example 2 Sem micrograph of the product of Example 1.
Figure 4:
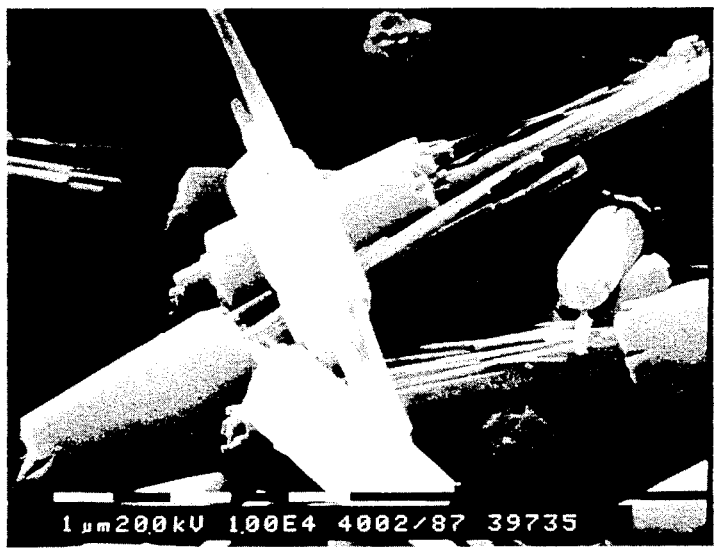
FIG. 4: SEM micrograph of the product of Example 2.

Comparative X-ray diffractograms of the products of Examples 1 and 2 are given in FIG. 1 and FIG. 2 respectively. In FIG. 2 E represents the peak positions of zeolite-erionite and W represents the peak positions of zeolite-W. SEM micrographs (magnification 10000 ×) of the products of Examples 1 and 2 are given in FIGS. 3 and 4 respectively.

EXAMPLE 3 (COMPARATIVE)

A synthesis gel with a molar composition of:

3.6 K$_2$O/0.36 Cs$_2$O/Al$_2$O$_3$/10 SiO$_2$/161 H$_2$O was prepared and crystallised for 48 hrs at 150° C. in a teflon lined 300 ml autoclave. XRD showed that the product was largely contaminated with zeolite pollucite.

EXAMPLE 4

A synthesis gel with a molar composition of:

2.35 K$_2$O/0.5 CsCl/Al$_2$O$_3$/10 SiO$_2$/161 H$_2$O and containing 9 ppm of Mg$^{2+}$ was crystallised for 65 hrs at 150° C. in a stainless steel autoclave. The product yield after washing and drying was 15.4%. XRD showed that the product was pure zeolite-L, the XRD-crystallinity versus the standard was 63%. SEM showed that the product consisted of cylindrical crystals with a length between 0.4 and 0.8 microns and with a diameter between 0.2 and 0.4 microns. The elemental analysis of the product (weight %) was K=12.0, Cs=4.3, Al=9.1 and Si=27.6. The molar composition of the product was 0.91 K$_2$O/0.09 Cs$_2$O/Al$_2$O$_3$/5.9 SiO$_2$.

EXAMPLE 5 (COMPARATIVE)

The procedure of Example 4 was repeated without Mg$^{2+}$. Again, the product was contaminated with zeolite erionite and with zeolite-W. SEM micrographs showed that the erionite, as in Example 2, was intergrown with the L-crystals.

The toluene adsorption capacities of the products of Examples 4 and 5 were measured. The results are given below:

| Toluene adsorption at 30° C. and at p/p$_0$ = 0.25 | | | |
|---|---|---|---|
| | wt % toluene | | |
| Example | adsorbed | desorbed | micropore capacity |
| 4 | 10.18 | 0.47 | 9.71 |
| 5 | 6.72 | 0.06 | 6.66 |

The low toluene capacity of Example 5 reflects the poor quality of the zeolite product prepared without Mg$^{2+}$-species.

What is claimed is:

1. A process for the preparation of a zeolite L containing caesium in which said zeolite L is crystallised from a synthesis mixture with a molar composition (expressed as oxides) of:
K$_2$O/SiO$_2$: 0.15 to 0.40
K$_2$O/Cs$_2$O: 3 to 10
H$_2$O/K$_2$O: 40 to 100 and
SiO$_2$/Al$_2$O$_3$: 7 to 13
and containing at least 0.5 ppm (by weight) of divalent metal cations in an effective amount to obtain substantially only zeolite L by limiting the formation of pollucite, erionite and zeolite W.

2. A process according to claim 1 wherein the synthesis mixture is obtained from the admixture of two solutions, Solution A comprising (1) KOH or $K_2O$, (2) $CsOH.H_2O$ or CsX where X is a halogen or nitrate, (3) Al $(OH)_3$ and (4) water and Solution B comprising (1) silica, (2) a divalent metal salt and (3) water.

3. A process according to claim 2 wherein the temperature of crystallisation is at least 130° C.

4. A process for the preparation of a zeolite L containing caesium in which siid zeolite L is crystallised from a synthesis mixture with a molar composition (expressed as oxide) of:

$K_2O/SiO_2$: 0.18 to 0.36
$K_2O/Cs_2O$: 4 to 7
$H_2O/K_2O$: 70 to 90 and
$SiO_2/Al_2O_3$: 8 to 12 and containing 0.5 to 15 ppm (by weight) of divalent metal cations in an effective amount to obtain substantially only zeolite L by limiting the formation of pollucite, erionite and zeolite W.

5. A process according to claim 4 wherein the synthesis mixture is obtained from the admixture of two solutions, Solution A comprising (1) KOH or $K_2O$, (2) $CsOH.H_2O$ or CsX where X is a halogen or nitrate, (3) $Al(OH)_3$ and (4) water and Solution B comprising (1) silica, (2) a divalent metal salt and (3) water.

6. A process according to claim 5 wherein the temperature of crystallisation is at least 130° C.

* * * * *